United States Patent [19]
Preikschat et al.

[11] Patent Number: 5,627,330
[45] Date of Patent: May 6, 1997

[54] LEVERAGE INSERTION ASSEMBLY

[75] Inventors: Ekhard Preikschat, Bellevue; Robert J. Hilker, Bothell, both of Wash.

[73] Assignee: Appa Systems, Inc., Bellevue, Wash.

[21] Appl. No.: 624,982

[22] Filed: Mar. 29, 1996

Related U.S. Application Data

[63] Continuation-in-part of Ser. No. 525,945, Sep. 8, 1995, Pat. No. 5,600,058.
[51] Int. Cl.$^6$ .................................................. G01N 11/14
[52] U.S. Cl. ............................................ 73/866.5; 73/54.29
[58] Field of Search ........................... 73/863.81, 863.82, 73/863.85, 863.26, 866.5, 86, 54.35, 54.29

[56] References Cited

U.S. PATENT DOCUMENTS

| | | | |
|---|---|---|---|
| 3,572,086 | 3/1971 | Johnston | 73/54.32 |
| 4,062,226 | 12/1977 | Hietala | 73/54.23 |
| 4,077,251 | 3/1978 | Winter | 73/54.35 |
| 4,175,425 | 11/1979 | Brookfield | 73/54.28 |
| 4,177,676 | 12/1979 | Welker | 73/866.5 X |
| 4,327,586 | 5/1982 | Goddard | 73/866.5 |
| 4,631,967 | 12/1986 | Welker | 73/863.82 X |
| 4,841,787 | 6/1989 | Waterman | 73/866.5 |
| 4,878,378 | 11/1989 | Harada | 73/54.35 |
| 5,174,325 | 12/1992 | Okel et al. | 73/866.5 X |
| 5,349,848 | 9/1994 | Driver | 73/54.28 |

*Primary Examiner*—Michael Brock
*Attorney, Agent, or Firm*—Dean A. Craine

[57] ABSTRACT

A leverage insertion assembly for inserting and removing an element from a main pipeline in which a fluid is flowing. The leverage device includes a hollow positioning pipe connected to the main pipeline with a gate valve attached to the positioning pipe. Formed on the outer surface of the section of positioning pipe on the opposite side of the gate valve from the main pipeline is a spiral cut-out. Handles attached at one end to the element located inside the positioning pipe extend through the spiral cut-out. During operation, the element is moved longitudinally inside the positioning pipe when the element is rotated by turning the handles. As the handles are turned, the cut-out limits the longitudinal movement of the element inside the positioning pipe. When the element has been moved a sufficient distance inside the positioning pipe to clear gate valve, the gate valve may be closed thereby closing the positioning pipe. The element can then be removed from the positioning pipe.

3 Claims, 6 Drawing Sheets

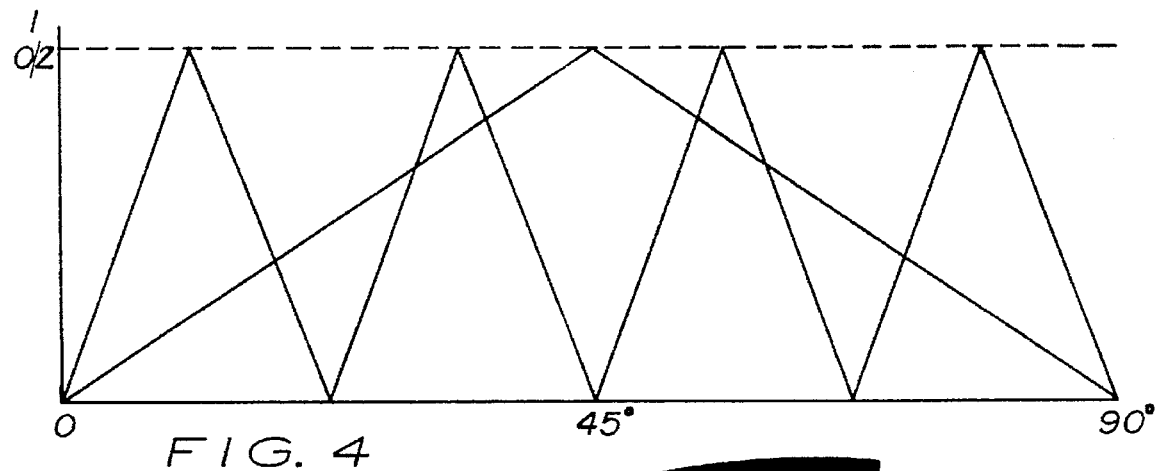
FIG. 4
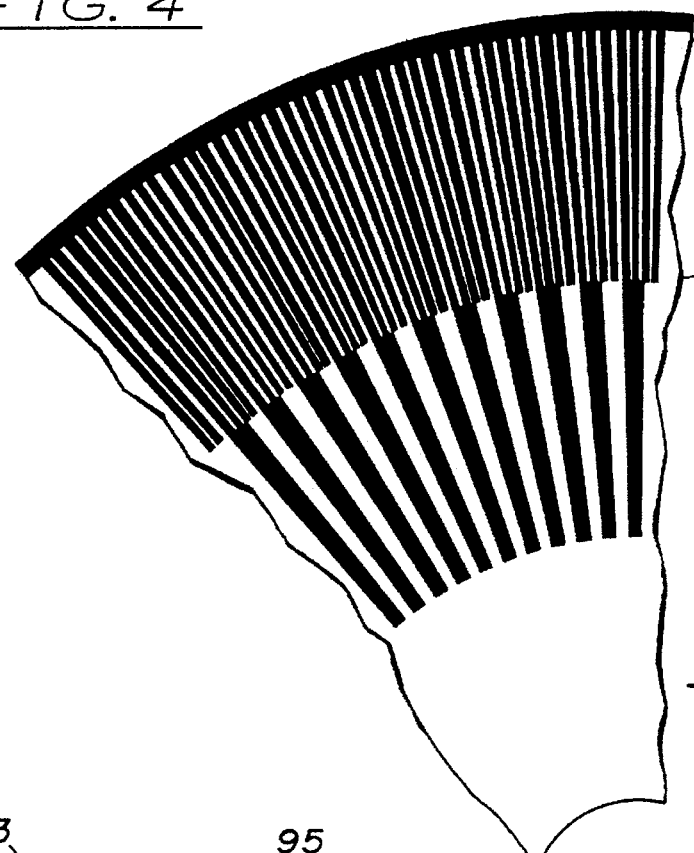
FIG. 5
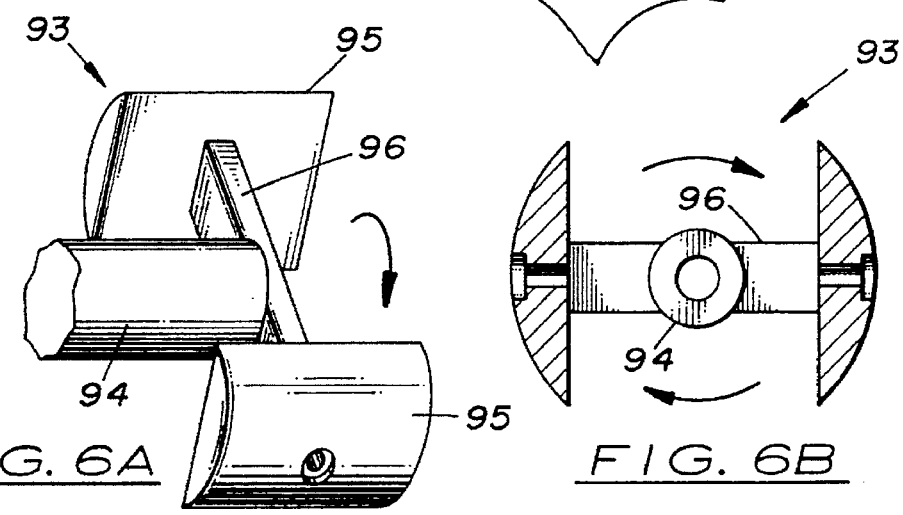
FIG. 6A
FIG. 6B

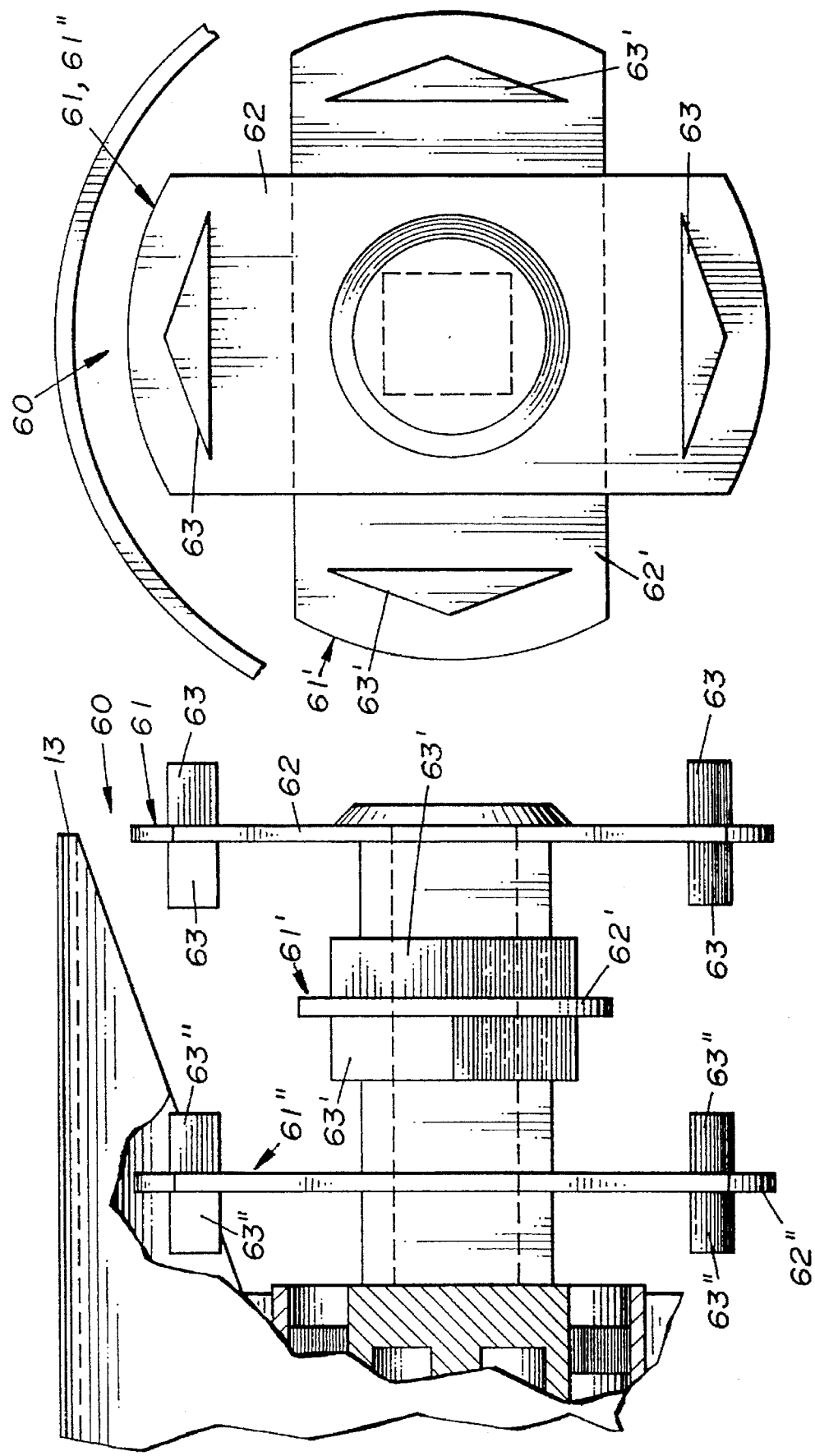

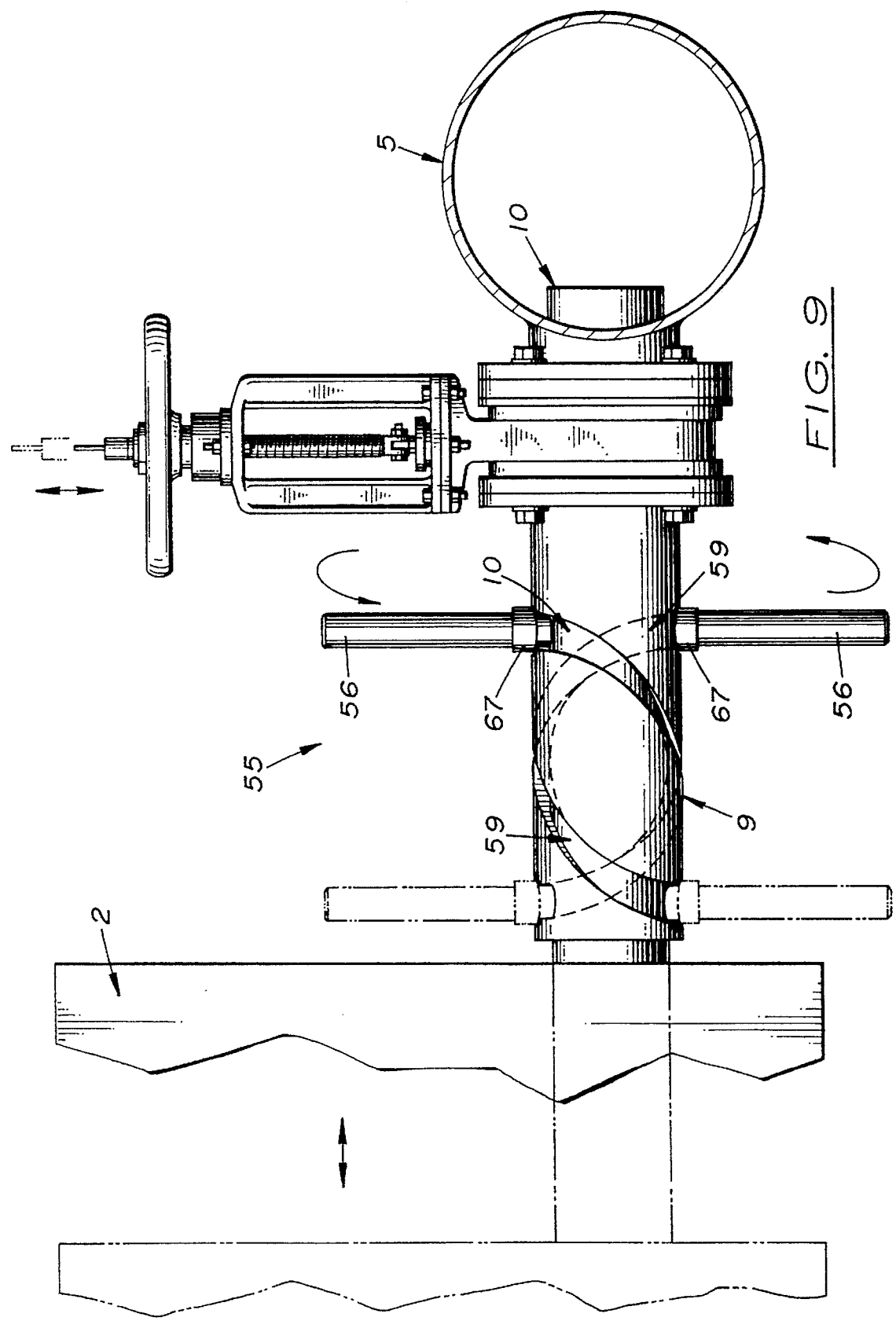

5,627,330

LEVERAGE INSERTION ASSEMBLY

This is a continuation-in-part application of a application, Ser. No. 08/525,945, filed on Sep. 8, 1995, U.S. Pat. No. 5,600,058.

BACKGROUND OF THE INVENTION

1. Field of the Invention

The present invention is directed to a rotating torque measurement, and more specifically the use of a torque measurement to determine the consistency of a pulp slurry, the viscosity of a fuel oil, or in the mining industry, the concentration of a mining slurry in a grinding circuit.

2. Description of the Related Art

In the pulp and paper industry, the preparation and control of a pulp stream depends directly on the consistency of the moving pulp slurry. For example, the addition of bleaching additives, of retention aides, of various filler, starches and additives is all based on the consistency of pulp slurry. To date, the most accurate measurement of consistency is still based on a mechanical measurement of the shear forces exerted by the moving pulp stream on a sensing element.

Large boats and freighters are typically powered by large, oil-fired industrial boilers which use low grade, bunker fuel oils as the primary fuel. Bunker fuel oils are the residual grades of the petroleum distillation process and can have a very high viscosity. These types of fuel oils can only be injected into a boiler if they are pre-heated to sufficiently reduce their viscosity. The efficiency of the burning process directly depends on how well the bunker fuel oil can be made into a mist and how uniformly it can be injected into the boiler—both of these factors depend on the viscosity of the bunker fuel oil.

It has been found that both pulp consistency and fuel-oil viscosity can be determined by measuring the torque on the shaft of a rotating impeller. When consistency (or viscosity) increases, the shear forces on the rotating impeller increases and it takes a higher driving force (torque) to rotate the impeller. Commercial devices are available to affect such a measurement, such as a consistency transmitter type MEK-41 manufactured by BTG, a Swedish company, and a rotating viscosity meter manufactured by Brookfield, a U.S.A. company. The former device uses a sensing shaft concentrically mounted within a drive shaft. A shear force measuring element (impeller) is mounted on the exposed end of a "sensor shaft" which is positioned directly into the moving pulp stream or fuel-oil. The sensor shaft rotates with the same rotational velocity as the outer shaft and is loosely coupled thereto. The outer shaft provides the main rotational driving force to the impeller and shields the sensor shaft from the frictional forces between the drive shaft and the outer gasket material, which prevents the pulp slurry from entering the housing of the sensor unit.

In a typical implementation, the relative rotational motion between the inner sensor shaft and the outer drive shaft is sensed and a counter-torque is applied to the sensor shaft so that it will rotate at exactly the same rotational velocity as the drive shaft. This counter-torque is equal and opposite to the torque on the sensor shaft produced by the shear forces of the pulp slurry on the rotating impeller. In the prior art, this counter-torque is not based on an absolute measurement of torque, but rather on secondarily deduced factors as measured by an electronic transducer or a rotating pneumatic transducer operating on the flapper-nozzle principle.

While this technology has long been used and accepted by industry as the best and most accurate method of measuring consistency, it has two fatal draw-backs—lack of durability and reliability. A pulp slurry is very abrasive and corrosive. This means the gasket materials used to isolate the rotating shafts have a finite lifetime, measured in months, and when one of the gaskets fails, the entire device can fail catastrophically. Pulp slurry will then penetrate to the interior of the sensing housing and damage the sensitive elements. When a critical pulp consistency transmitter fails, the computerized process control loop goes out of control and the production line has to be shut down. For a large paper machine, the cost of such a forced shutdown is measured in the thousands of dollars per work shift. Therefore, it is important to provide a means to maintain and service a pulp consistency transmitter without having to shut down production.

Even though this invention makes specific reference to a pulp slurry and fuel oil, it should be understood that it also applies to a variety of other materials, such as natural and synthetic fibers like cotton, wool and kevlar fibers, as well as many other kinds of fluids, such as molasses in the crystallization process leading to the production of refined sugar.

SUMMARY OF THE INVENTION

It is, therefore, a general object of the present invention to provide an improved rotating consistency transmitter which is based on an absolute measurement of torque to allow for easy calibration both under laboratory as well as production conditions, and furthermore a device which incorporates certain features to make it very rugged for use in a corrosive and abrasive environment.

It is an object of the invention to provide such a transmitter which can be used, installed, serviced and dismounted without having to shut down a production line.

It is a further object of the invention to allow use of a transmitter which enables the measurement of torque to be linearized with increasing consistency.

It is a still further object of the invention to provide a method for accurately and predictably measuring the viscosity or consistency of a flowing multi-phase materials, such as a pulp slurry, in a pipeline.

These and other objects of the invention are met by providing a rotating consistency transmitter designed to measure the consistency, concentration or viscosity of a multi-phase material located in a container or flowing in a main pipeline by measuring the torque applied on a composite, torque detecting, rotating shaft. The rotating shaft comprises three concentrically aligned shafts—an outer drive shaft, a middle sensor shaft and an inner reference shaft. The three shafts are aligned and connected together so that when the outer drive shaft is rotated, the sensor shaft is rotated which, in turn, causes the reference shaft to rotate. In the preferred embodiment, the distal end of the outer drive shaft is attached to a rotating means capable of rotating the rotating shaft at a defined rotation speed. The proximal end of the reference shaft is connected to a force detecting means disposed inside the main pipeline. During operation when slurry is flowing through the main pipeline, rotation of the force detecting means is impeded thereby producing a twisting action on the sensor shaft. This twisting action produces a torque which is predictable and absolutely calibratable. The reference shaft, sensor shaft and drive shaft are isolated from the slurry.

Attached to the transmitter is a torque detecting means capable of detecting the amount of torque applied to the sensor shaft. In the preferred embodiment, the amount of torque is determined by measuring the angular displacement between the distal and proximal ends of the sensor shaft. This angular displacement is measured by passing a focussed light beam across two closely aligned, transparent optical disks. Each optical disc has a plurality of opaque lines created thereon designed to prevent passage of light therethrough. One optical disk is attached to the distal end of the sensor shaft via the drive shaft while the other optical disk is attached to the distal end of the sensor shaft via the reference shaft. During operation, a focused beam of light is transmitted through the optical disks. The amount of light transmitted therethrough is a direct measurement of the torque acting on the sensor shaft.

As mentioned above, in one embodiment, the transmitter is attached to pipeline containing a flowing slurry. The transmitter is housed inside a carrying pipe which is selectively connected to the main pipeline via a positioning pipe. During assembly, the carrying pipe is inserted to the positioning pipe and attached thereto. An optional valve means is also provided which enables the positioning pipe to be selectively opened or closed thereby allowing the transmitter to be easily installed or removed from the main pipeline.

Using the above described transmitter, a method of measuring the consistency of a flowing liquid in a main pipeline is also provided.

BRIEF DESCRIPTION OF THE DRAWINGS

FIG. 4 is a diagram showing the relationship between the amount of light transmitted across the two optical disks and the amount of angular displacement.

FIG. 5 is a front plan view of an optical disk with a high density of opaque lines manufactured thereon.

FIG. 6A is a side elevational view of a two, semi-circular bladed impeller.

FIG. 6B is a front elevational view of the two, semi-circular bladed impeller shown in FIG. 6A.

FIG. 7A is a side elevational view of a three-bladed impeller.

FIG. 7B is a front elevational view of the three-bladed impeller shown in FIG. 7A.

FIG. 9 is a side elevational view of the extraction device which allows the impeller to be extracted past the gate valve.

DESCRIPTION OF THE PREFERRED EMBODIMENT(S)

The present invention in one embodiment finds preferred usage as a rotating consistency transmitter 2 in the pulp and paper industry. In a typical application in the bleach plant of a paper mill, the rotating consistency transmitter 2 is installed just prior to the chlorination stage, where the addition of chlorine to the pulp is critically controlled based on the amount of dry fiber flow. The amount of dry fiber flow is determined by the pulp flow velocity and the pulp consistency. The amount of chlorine added to the flowing pulp slurry determines how much the pulp gets bleached and also the residual amount of chlorine left after the bleaching stage. If the residual chlorine level is too high, this can lead to the formation of dioxin in the paper and also to the discharge of free chlorine into the atmosphere. Both conditions, of course, are undesirable.

Figure 1:
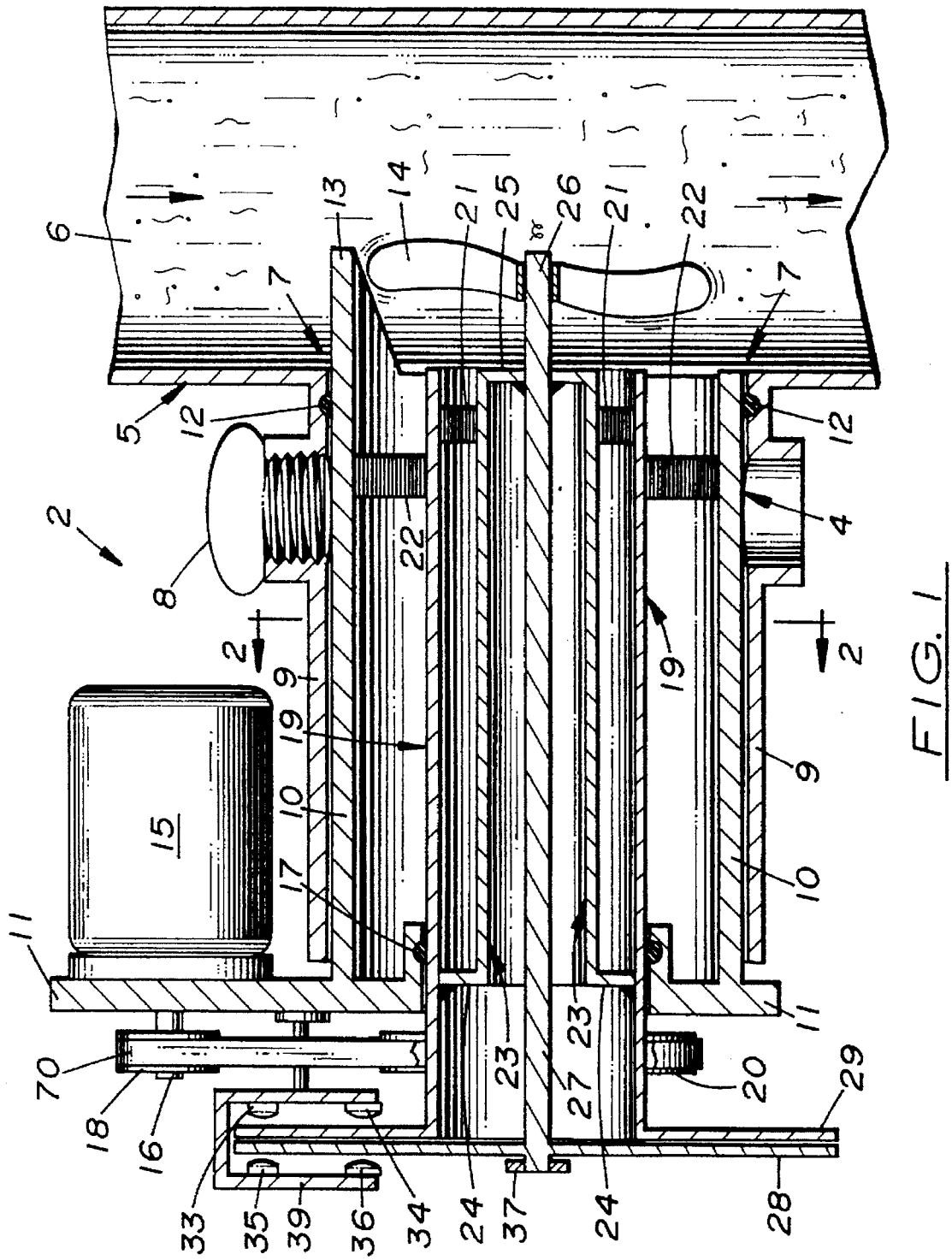
FIG. 1 is a sectional, side elevational view of the rotating consistency transmitter disclosed herein.

FIG. 1 shows the rotating consistency transmitter 2 comprising a carrying pipe 10 installed on the side of a main pipeline 5 which is transporting a pulp slurry 6 flowing in a downward direction. A side port 7 is formed on the side of the main pipeline 5 over which a positioning pipe 9 is attached. The positioning pipe 9 is hollow with an inner passageway, an outer distal opening, and an outer surface. The longitudinal axis of the positioning pipe 9 is aligned perpendicularly with the longitudinal axis of the main pipeline 5 and is designed to hold a hollow, longitudinally aligned, snug-fitting, carrying pipe 10. An optional gate valve 8 may be attached to the positioning pipe 9 which enables the positioning pipe 9 to be selectively opened or closed. As discussed further below, this feature enables the carrying pipe 10 to be selectively positioned or removed from the positioning pipe 9 for maintenance without requiring the fluid flow through the main pipeline 5 to be discontinued.

Attached to the distal end of the carrying pipe 10 is a drive plate 11 designed to hold the rotating means. The drive plate 11 partially extends into the central area of the carrying pipe 10 thereby acting as a support and an alignment surface for the drive shaft 19. First and second O-ring seals 12, 17 are disposed between the positioning pipe 9 and the carrying pipe 10 to create a water-tight seal therebetween. Formed on the proximal end of the carrying pipe 10 is a lip structure 13 which extends into the main pipeline 5 and is designed to protect the rotating impeller 14 from the flowing pulp slurry 6.

In the preferred embodiment, the rotating means is a fractional horsepower motor 15 mounted to the drive plate 11. The motor's drive shaft 16 has a motor drive shaft sprocket 18 mounted thereon which, in turn, rotates a belt 70 and powers the large diameter sprocket 20. The large diameter sprocket 20 is directly connected to the distal end of the drive shaft 19. When the motor 15 is operated, the belt 70 turns the sprocket 20 which, in turn, rotates the drive shaft 19.

Longitudinally aligned and positioned inside the carrying pipe 19 is a sensor shaft 23. The sensor shaft 23 has a flange surface 24 formed at the distal end thereof and a closed end surface 25. The flange surface 24 is welded to the inside surface of the carrying pipe 19. The configuration provides a barrier to keep the slurry 6 from entering the electronic area adjacent to the transmitter 2.

Longitudinally aligned and positioned inside the sensor shaft 23 is a reference shaft 27. The distal end of the reference shaft 27 is attached to the first optical disk 28 discussed further below. The proximal end of the reference shaft 27 is welded and extends through the end surface 25 on the sensor shaft 23. A force detecting means, such as an impeller 14, is mounted to the portion 26 of the reference shaft 27 that extends into the main pipeline 6.

A first gasketed rotating seal 21 is positioned between the inside surface of the drive shaft 19 and the outside surface of the sensor shaft 23. A second gasketed rotating seal 22 is positioned between the outside surface of the drive shaft 19 and the inside surface of the carrying pipe 10. When slurry 6 is flowing in the main pipeline 5, the first and second seals 21, 22 prevent slurry 6 from getting between the sensor shaft 23 and the drive shaft 19 and between the drive shaft 19 and the carrying pipe 10, respectively.

It is important to note that while the first gasketed rotating seal 21 is stationary with respect to both the drive shaft 19 and the sensor shaft 23, the second gasketed rotating seal 22 is positioned between two surfaces, which are rotating with respect to each other. The whole reason for introducing the drive shaft 19 is to prevent the frictional forces between the rotating drive shaft 19 and the stationary carrying pipe 10 from influencing the torque measurement across the sensor shaft 23. All frictional forces are taken up by the second seal 22 and are decoupled from the operation of the sensor shaft 23.

As mentioned above, the sensor shaft 23 is welded at its distal end to the inside surface of the drive shaft 19. During operation, shear forces acting on the impeller 14 cause a torque to act over the whole length of the sensor shaft 23, which produces a slight twisting action thereon. This twisting action is monitored by a reference shaft 27 which is welded to the inside surface of the proximal end of the sensor shaft 23. By fastening one first disk 28 to the distal end of the reference shaft 27 and a second disk 29 to the distal end of the drive shaft 19, respectively, one can directly observe the twist over the full length of the sensor shaft 23. In particular, it should be noted that the extent of the twisting action is a direct measure of the torque acting on the sensor shaft 23 and is an absolute quantity that can be directly related to the physical parameters of the sensor shaft 23, (i.e. the length, inner and outer diameters, material of construction, and its modulus of rigidity).

The relationship between torque and twisting action can not only be expressed in concise mathematical terms but also by a straightforward empirical measurement, e.g. by holding one end of the sensor shaft 23 rigid, while applying a known amount of torque to the opposite end. This procedure can be easily repeated for different shafts to check the response of each shaft to a known amount of torque. In other words, if one holds the physical parameters of the sensor shaft 23 within tight specifications, one is able to measure the applied torque in absolute terms simply by measuring the amount of twisting action on the sensor shaft 23.

As shown in FIG. 1, the first and second optical disks 28, 29 are mounted to the ends of the reference shaft 27 and drive shaft 19, respectively. Two focussed laser diodes 33, 34 are radially mounted on a converted, U-shaped bracket 39 disposed over the peripheral edges of the disks 28, 29. The diodes 33, 34 are mounted on the bracket 39 along one side of the first and second optical disks 28, 29. Two respective light sensing photo diodes 35, 36 are mounted radially on the opposite side of the bracket 39 on the opposite side of the optical disks 28, 29. A mounting nut 37 is used to fasten the first optical disk 28 to the end of the reference shaft 27.

Figures 2, 3:
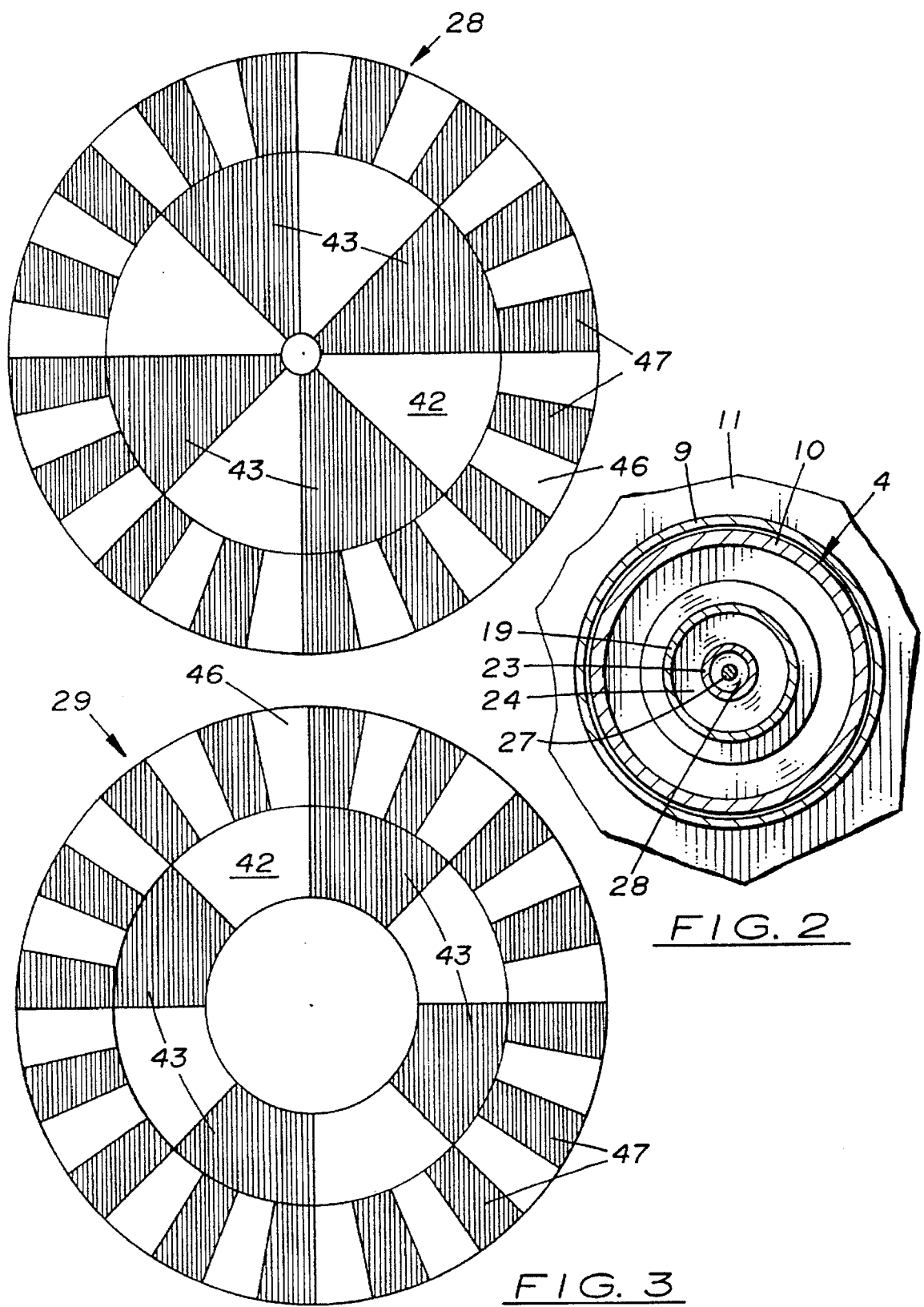
FIG. 2 is a sectional, front elevational view taken along Line 2—2 in FIG. 1.
FIG. 3 is a front plan view of the first and second disks.

FIG. 3 is a front elevation view of the two complementary first and second optical disks 28, 29, respectively. Optical disks 28, 29 are made of rigid, transparent material, such as glass or acrylic material with an inner circle area 42 having four opaque lines 43 and an outer circle area 46 having sixteen opaque lines 47. When initially installed on the transmitter 2, the positions of the optical disks 28, 29 are adjusted so that no light is transmitted across the two-disk interface. Then, when a torque is applied to the sensor shaft 23, the first and second optical disks 28, 29 are displaced with respect to the other, thereby allowing a certain amount of light to be transmitted in direct proportion to the amount of angular displacement of one disk with respect to the other. The maximum transmitted light intensity is $0.5 I_o$, where $I_o$ is the full light output from the laser diode. This effect is linear up to a certain angular displacement, which depends on the number of lines on the disk's inner and outer circle areas 42, 46, respectively. Using this embodiment, the amount of light transmitted across the two optical disks, shown in FIG. 4, will be linear and will reach the maximum value (of $I_o/2$) for a displacement of 45° for the inner circle area 42 and 11.25° for the outer circle area 46. The corresponding amount of transmitted light is shown in FIG. 4 as a function of angular displacement. Obviously, by adding more opaque lines, one can increase the accuracy of this measurement.

With high resolution photo-etching techniques, it is possible to create many more lines on the optical disks as shown in FIG. 5. Let us assume a line density for the outer pattern of one line per degree or a full range of light transmission from 0 to $I_o/2$, over 0.5 degree of angular displacement.

Let us assume we use 360 optical lines per revolution, i.e. 1 line per 1° of angular displacement, then for an optical disk of 7.5 cm (3") diameter, the thickness of each line is equivalent to 0.5°, or about 33 micron in width. This means if we use a laser diode focussed down at the plane of the optical disk to produce a line measuring 33 microns (in width) by 2,000 microns (in length—aligned radially parallel to the lines) one can accurately measure the amount of rotational displacement (of one disk with respect to the other) to a resolution of better than 0.01°.

Let us further assume that the sensor shaft 23 is 20 inches long with an outer diameter of 12.7 mm 0.5 inches) and a wall thickness of 0.89 mm (0.035 inches). Then one can exactly calculate the amount of angular displacement "q" for a maximum amount of torque T as follows:

$q=(32\ T\ L)/(3.14\ (D_o^4-D_i^4)G)$, measured in radians, where:

T=torque=13 inch-pounds max

L=length of the sensor shaft=20 inches $D_o$=outer diameter of the sensor shaft=0.5 inches $D_i$=inner diameter of the sensor shaft=0.43 inches and, G=modulus of rigidity of titanium=$5.6 \times 10^6$ psi.

With these parameters, using type II titanium alloy and a torque of 13 inch—pounds, the maximum amount of angular displacement is 0.034 radians, or about 2°. The beauty of this type of measurement is that it is an absolute measurement of torque and only depends on the dimensions and the material of the shaft, i.e. the modulus of rigidity of the titanium shaft of the specific dimensions. The angular displacement of the sensor shaft 23 can be accurately calculated and even more accurately measured using static measuring techniques.

Another important advantage of this type of configuration is that (i) the structural integrity of the concentric shafts 19, 23, 27 is fully preserved, and (ii) there is no relative free motion between the outer and inner shafts 19, 27, respectively. These are two important benefits over the technology commonly used today, where the survivability of the whole system depends on the integrity of the first rotating seal 21 between the drive shaft 19 and the sensor shaft 23. In the prior art, a break in this seal 21 leads to the catastrophic failure of the whole system, whereas in the herein described invention, a break in the seal 21 merely allows some of the slurry 6 to leak between the sensor shaft 23 and the drive shaft 19. As there is no relative motion between the two shafts 19, 23, the effect of a leak has a negligible effect on the measurement.

Referring back to FIG. 1, it should be noted that the configuration of the positioning pipe 9 and the carrying pipe 10 is such that it allows the impeller 14 to be pulled back out of the slurry stream far enough to be extracted past the gate valve 8. Once the impeller 14 clears the gate valve 8, the gate valve 8 can be shut, thereby allowing the rotating consistency transmitter 2 to be removed from the positioning pipe 9 without having to shut down the production line. This is an important advantage in cases where it is important to maintain a constant production cycle.

The shape of the rotating impeller 14 determines how the impeller interacts with the fluid flow. If the impeller takes the form of a flat disk rotating about its common axis, it will preferentially measure the frictional forces on the flat surface of the disk. If it is instead a cylinder rotating within a larger, stationary, outer cylinder, it will preferentially measure the viscosity forces between the moving surface relative to the stationary surface.

When the impeller rotates within the pulp slurry, there are several forces acting on the impeller: (1) the yield stress forces that result when a moving object causes a separation (or break-up) of the fibers within an interlocking fiber network (also referred to as "coherent flocculation"); (2) the frictional forces caused by the moving fiber stream pressing against the flat surface of the impeller; and, (3) the turbulence forces caused by the wake of the moving impeller.

The Type (1) force is described in greater detail in *The Flocculation of Pulp Fibres, Papermaking Raw Materials*, R. J. Kerekes et al., Transactions of the 8th Fundamental Research Symposium held at Oxford, England, September, 1985, published by Mechanical Engineering Publ., Ltd. London, pps. 265–310. The authors describe the forces which act to give a fibre network its mechanical strength and how the tensile strength (or yield stress) of a fiber network is directly related to pulp consistency.

It should be noted that the other two forces of Type (2) and (3) are not only related to pulp consistency, but also to a number of variables, which, under process conditions, are typically not known or controlled.

The Type (2) force is like a classical frictional force and has the form: $F_f = \mu A N$, where $\mu$ is like the coefficient of friction, A is the surface area of the impeller, and N is the normal force per surface area and is related to the amount of pulp fibers carried within the pulp slurry. The coefficient of friction depends on a number of uncontrolled variables: (i) the viscosity of the carrying fluid (water) which depends on fluid temperature and hardness of it, i.e. the amount of mineral content; (ii) the smoothness of the surface structure of the impeller, and; (iii) the thickness of the water layer between the impeller surface and the moving pulp slurry, which acts as a lubricant.

The Type 3 force depends on (i) the fluid flow velocity, (ii) the size and rotational speed of the impeller, which determines the size of the wake left behind by the impeller blades, and (iii) the consistency of the pulp. When the pulp consistency drops below 1%, there are not enough fibers present in the flow to dampen the flow vortecies and turbulences set up behind the rotating impeller blades.

From these considerations, it is clear that for measuring pulp consistency, the best type of impeller is one that maximizes forces of Type 1 and minimizes forces of Types 2 and 3. In other words, it is best to have an impeller that has a front edge of maximum size with the smallest surface area. A simple piano wire positioned so that its major axis is perpendicular to the flow would be an idealized implementation of such a geometry. FIGS. 6A and 6B show a more realistic implementation of an impeller 93 for measuring pulp consistency, comprising two, semi-circular blades 95 mounted to a common support post 96, which, in turn, is fastened to shaft 94.

Kerekes et. al. (Ref.: *Motion of Pulp Fibre Suspensions in Rotary Devices*, C. P. J Bennington, R. J. Kerekes, and J. R. Grace, The Canadian Journal of Chemical Engineering, Vol. 69, February 1991, page 251–258) have shown that, to a first order approximation the torque resulting from the shear forces of a pulp slurry acting on a rotating impeller has a relationship that is somewhere between a square law and a cube law with consistency. This means that for higher consistencies, above 8%, the shear forces are so high that even with a relatively small impeller, with a 3.5" diameter, the torque can easily be measured. However, at smaller consistencies, below 3%, the shear forces are relatively small. With the above-described gate-valve 8 configuration, the maximum diameter of the impeller is determined by the maximum opening size of the gate valve 8.

FIGS. 7A and 7B show another embodiment of the force detecting means including a stacked, three bladed impeller 60. The impeller 60 has three blades 61, 61', and 61" stacked side by side each other with each successive impeller being rotated 90°, so that the slurry can flow freely between the neighboring blades. Each blade 61, 61', 61" comprises a thin, rectangular-shaped plate 62, 62', 62", respectively, with two pairs of separating wings 63, 63', 63" at each side of the plate at opposite ends. A square-shaped mounting hole is also provided which enables the impeller 60 to fit onto a complementary shaped reference shaft.

FIG. 1 shows an optional flow breaker lip structure 13 located at the end of the carrying pipe 10. This lip structure 13 breaks up the pulp flow in front of the impeller(s) and reduces the influence of the velocity of the pulp slurry 6. It also protects the impeller 14 from the impact of dried pulp slugs, which can destructively impact anything positioned inside the flow line. The size and shape of this lip structure 13 depends on the consistency of the pulp flow and the number of impeller blades. In some instances, it may in fact be preferable to mount the lip structure 13 some distance upstream from the impeller 14 in order to minimize the amount of dewatering of the pulp prior to the measuring region, which could give erroneous readings of consistency.

According to the Handbook of Chemistry and Physics (published by: The Chemical Rubber Publishing Co., 1961, page 2194) the viscosity of a substance is defined as "the tangential force per unit area of either of two horizontal planes at unit distance apart, one of which is fixed, while the other moves with unit velocity, the space being filled with the substance."

Figure 8:
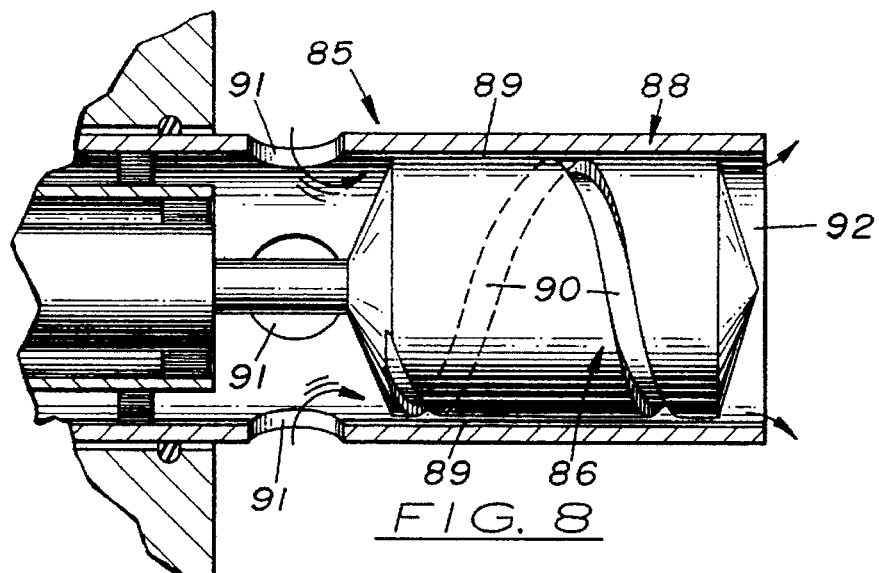
FIG. 8 is a side elevational view of the rotary viscosimeter.

FIG. 8 shows still another embodiment of the force detecting means comprising a rotary viscosimeter 85. The viscosimeter 85 is similar to the viscosimeter disclosed by Winter in U.S. Pat. No. 4,077,251 having an inner cylindrical shape 86 which rotates within a larger outside cylinder 88. The gap 89 between the cylindrical shape 86 and the cylinder 88 is constant. The cylindrical shape 86 and the cylinder 88 define the two horizontal planes, and the torque which has to be applied to the inner rotating cylinder 86 defines the tangential force referred to in the above-referenced definition. A narrow screw band 90 is attached to the outer surface of the cylindrical shape 86 to draw fluid in through holes 91 located in the outer cylinder 88 along the gap 89 and out through the opening 92 on the cylinder 88 back into the primary flow. This ensures that the fluid substance within the cylindrical shape 86 and the cylinder 88 is continually being exchanged.

To linearize the measurement of consistencies ($C_y$) over a wide range of readings, it is necessary to apply a fractional root function to the raw torque reading (t), as follows:

$$C_y = a \cdot \tau^{-1/b}$$

where "a" is a constant and "b" is a factor between 2 and 3. In the simplest form, "b" is 2, and the consistency is simply obtained by using a square root conversion circuit using an 'integrated circuit multiplier' type AD532 from Analog Devices, or similar (ref.: 1992 Special Linear Reference Manual, published by Analog Devices). The same device can also be used to obtain a cube root function or various combinations in between.

FIG. 9 shows a screw-feed leveraging device 55 which allows the rotating consistency transmitter 2 to be forcible and safely removed from the in-line position in the positioning pipe 9. It should be noted that some main pipelines operate up to a pressure of 10 bar, i.e. 150 psi. At 3.5 inch diameter, the cross-sectional area of such pipelines is 9.62 square inches, which, at 10 bar, results in a total pressure of 1,440 pounds of force. Removing the rotating consistency transmitter 2 from the main pipeline can be difficult and hazardous.

The leveraging device 55 includes two, long handles 56, threadingly attached at one end to the opposite sides of the carrying pipe 10. The two handles 56 extend through a spiral cut-out 59 formed in the positioning pipe 9. During use, the carrying pipe 10 is moved longitudinally inside the positioning pipe 9 by turning the handles 56, thereby causing them to follow the cut-out 59. The location, pitch and length of the cut-out 59 is sufficient so that the one rotation of the handles 56 causes the carrying pipe 10 to move a sufficient distance inside the positioning pipe 9 so that the impeller end of the carrying pipe 10 clears the gate valve 8.

Figure 10:
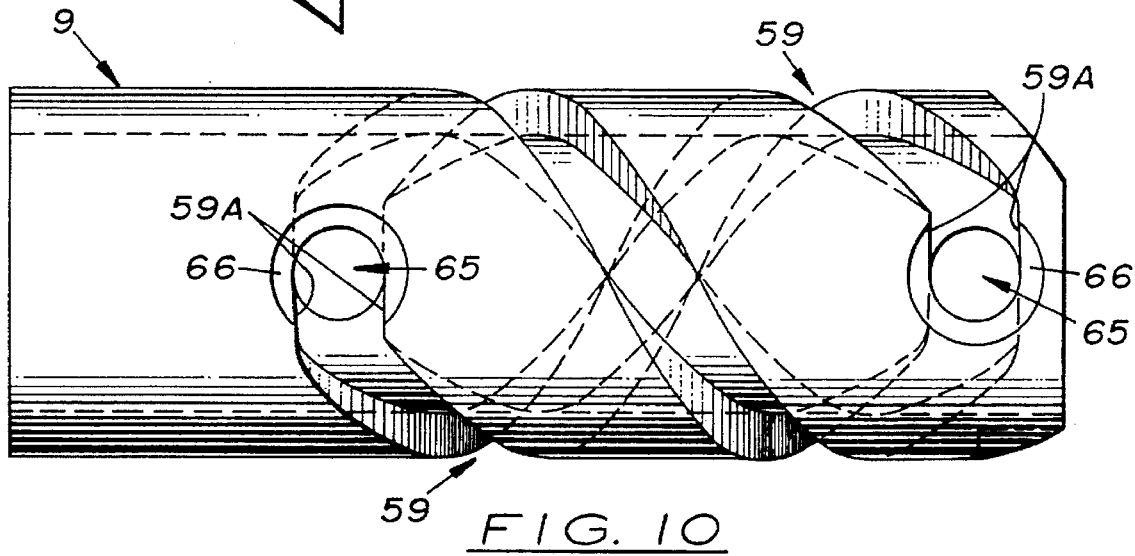
FIG. 10 is a side elevational view of the positioning pipe shown in FIG. 9 detached from the main pipeline with the carrying pipe removed.

The positioning pipe 9 is shown in greater detail in FIG. 10. The spiral cutout 59 has flat surfaces 59A manufactured on the distal and proximal ends thereof which act to prevent longitudinal movement of the carrying pipe 10 within the positioning pipe 9 when the handles 56 are being manually locked or unlocked in position on the positioning pipe 9.

Figure 11:
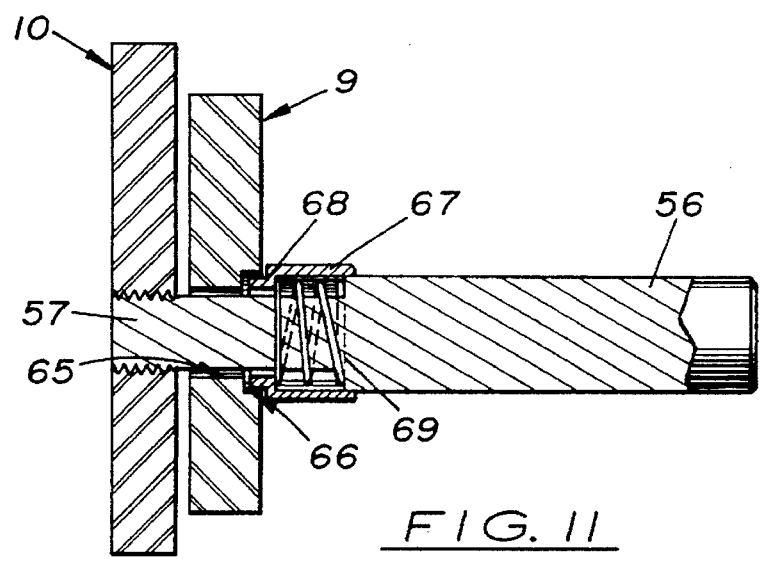
FIG. 11 is a sectional, side elevational view of the leverage insertion assembly showing the placement of the carrying pipe, positioning pipe, and the handle.

A locking means is provided for locking the handle 56 in position on the positioning pipe 9. In the embodiment shown in FIGS. 10 and 11, the locking means includes an outer bushing 67 that has a lower neck 68 that engages a recess surface 66 formed at each distal and proximal end of the spiral cut-out 59. A biasing spring 69 disposed between the bushing 67 and the handle 56 forces the bushing 67 inward to engage the recess surface 66 when handle 56 is properly aligned over the opening 65. When each bushing 67 is moved outward to disengage the recess surfaces 66, the handles 56 may be manually turned to follow the spiral cut-out 59. The end surfaces 59A formed on the spiral cutout 59 temporarily hold the carrying pipe 10 in position in the positioning pipe 9 so that the operator may be properly positioned for removing or attaching the carrying pipe 10 in the positioning pipe 9.

In this manner, the handles 56 are used both as a leveraging tool and as positioning tool to move the carrying pipe 10 inside the positioning pipe 9. When the carrying pipe 10 is longitudinally moved inside the positioning pipe 9 so that the impeller end of the carrying pipe 10 clears the gate valve 8, the handle on the gate valve 8 may be turned to close the gate value 8 thereby preventing slurry from flowing through the positioning pipe 9. The carrying pipe 10 and hence, the rotating consistency transmitter, can then be removed from the positioning pipe 9.

It should be recognized, by those skilled in the art, that the leveraging device 55 is a novel way of inserting any element used to measure or sample the material in an in-line pressurized flow, and has uses and applications that are not solely restricted to the herein described measuring technique. This particular leveraging device 55 represents a fifth generation design that has been evolved over a period of fifteen years by the current inventors in an on-going effort to provide a simpler and safer way of inserting a device into a fully pressurized line. Other possible uses for such a leveraging device 55 are the insertion of an optical measuring head to determine brightness, concentration, turbidity, index of refraction of a process fluid, as well as to allow for extraction of a sample of the fluid for purposes of laboratory testing.

Using the above described transmitter 2, a method for measuring the consistency of a flowing liquid in a pipeline is also disclosed. The method comprises the following steps:

a. selecting a consistency transmitter disclosed herein;

b. locating the consistency transmitter so that the force detecting means is placed into the slurry;

c. rotating said force detecting means in said slurry;

d. measuring the amount of light transmitted across said first and second optical disks;

e. determining the amount of torque across said sensor shaft based on the amount of light transmitted across said first and second optical disks; and, f. calculating the consistency of said slurry based on the torque measurement on said sensor shaft.

In compliance with the statute, the invention, described herein, has been described in language more or less specific as to structural features. It should be understood, however, the invention is not limited to the specific features shown, since the means and construction shown comprised only the preferred embodiments for putting the invention into effect. The invention is, therefore, claimed in any of its forms or modifications within the legitimate and valid scope of the amended claims, appropriately interpreted in accordance with the doctrine of equivalents.

We claim:

1. A leverage insertion assembly, for a main pipeline having a fluid flowing therethrough, said insertion assembly, comprising:

a. a positioning pipe connected to and communicating with the main pipeline, said positioning pipe having an inner passageway, an outer distal opening, and an outer surface;

b. a control valve connected to said positioning pipe to open or close said positioning pipe on the main pipeline;

c. a carrying pipe capable of being longitudinally disposed inside said positioning pipe and partially extended into the main pipeline;

d. a leverage means attached to said carrying pipe capable of longitudinally moving said carrying pipe inside said positioning pipe so that said carrying pipe may be extended into or retracted from said main pipeline and pass said control valve, said leveraging means includes positioning pipe having a spiral cut-out and at least one handle attached to said carrying pipe and extending through said cut-out, said handle capable of sliding along said cut-out when said handle is forcibly turned to rotate and longitudinally move said carrying pipe inside said positioning pipe.

2. A leverage insertion assembly, as recited in claim 1, further including a locking means disposed between said handle and said positioning tube for selectively locking said handle thereto.

3. A leverage insertion assembly, as recited in claim 1, wherein said element is a rotating consistency transmitter capable of determining the consistency of the fluid flowing in said main pipeline.

* * * * *